(12) United States Patent
Starobinets et al.

(10) Patent No.: US 11,759,110 B2
(45) Date of Patent: Sep. 19, 2023

(54) CAMERA VIEW AND SCREEN SCRAPING FOR INFORMATION EXTRACTION FROM IMAGING SCANNER CONSOLES

(71) Applicant: KONINKLIJKE PHILIPS N.V., Eindhoven (NL)

(72) Inventors: Olga Starobinets, Newton, MA (US); Sandeep Madhukar Dalal, Winchester, MA (US); Ranjith Naveen Tellis, Tewksbury, MA (US); Hareesh Chamarthi, Cambridge, MA (US); Yuchen Qian, Lexington, MA (US); Vijay Parthasarathy, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/097,306

(22) Filed: Nov. 13, 2020

(65) Prior Publication Data
US 2021/0145280 A1  May 20, 2021

Related U.S. Application Data

(60) Provisional application No. 62/936,741, filed on Nov. 18, 2019.

(51) Int. Cl.
*A61B 5/00* (2006.01)
*G06F 3/04847* (2022.01)
*G06F 3/04842* (2022.01)

(52) U.S. Cl.
CPC ........ *A61B 5/0013* (2013.01); *G06F 3/04842* (2013.01); *G06F 3/04847* (2013.01)

(58) Field of Classification Search
CPC .............. A61B 5/0013; G06F 3/04842; G06F 3/04847
See application file for complete search history.

(56) References Cited

U.S. PATENT DOCUMENTS

| | | | | |
|---|---|---|---|---|
| 6,497,661 | B1 * | 12/2002 | Brock-Fisher | A61B 5/0002 73/620 |
| 7,738,940 | B2 * | 6/2010 | Shoji | G16H 30/20 600/407 |

(Continued)

*Primary Examiner* — Jeremy L Stanley

(57) ABSTRACT

An apparatus (10) provides remote assistance to a local operator of a medical imaging device (2) disposed in a medical imaging device bay (3) via a communication link (14) from a remote location (4) that is remote from the medical imaging device bay to the medical imaging device bay. The apparatus includes a workstation (12) disposed at the remote location including at least one workstation display (24). At least one electronic processor (20) is programmed to, over the course of a medical imaging examination performed using the medical imaging device: extract successive image frames from video (17) or screen sharing (18) of a controller display (24') of the medical imaging device; screen-scrape information related to the medical imaging examination from the successive image frames over the course of the medical imaging examination; maintain status information on the medical imaging examination at least in part using the screen-scraped information; and output an alert (30) perceptible at the remote location when the status information on the medical imaging examination satisfies an alert criterion.

20 Claims, 2 Drawing Sheets

(56) References Cited

U.S. PATENT DOCUMENTS

| | | | | |
|---|---|---|---|---|
| 8,682,042 B1* | 3/2014 | Manion | G06Q 10/00 | 382/187 |
| 9,980,629 B2* | 5/2018 | King | A61B 1/00057 | |
| 10,297,343 B1* | 5/2019 | Wartenfeld | G16H 70/20 | |
| 10,824,898 B2* | 11/2020 | Lemay | G06T 3/4038 | |
| 10,845,948 B1* | 11/2020 | Lewis | G06F 3/0482 | |
| 11,222,103 B1* | 1/2022 | Gallopyn | G10L 17/22 | |
| 11,222,716 B2* | 1/2022 | Vozila | G06F 3/165 | |
| 11,227,679 B2* | 1/2022 | Owen | G16H 40/20 | |
| 11,398,033 B2* | 7/2022 | Kamon | A61B 1/0051 | |
| 2002/0112733 A1* | 8/2002 | Miyauchi | G16H 40/67 | 600/408 |
| 2007/0248261 A1* | 10/2007 | Zhou | G06T 19/006 | 382/154 |
| 2007/0282912 A1* | 12/2007 | Reiner | G16H 30/40 | |
| 2008/0058963 A1* | 3/2008 | Garibaldi | A61B 6/02 | 700/19 |
| 2008/0175460 A1* | 7/2008 | Reiner | G06F 16/26 | 707/E17.019 |
| 2008/0312963 A1* | 12/2008 | Reiner | G06Q 10/06398 | 705/7.42 |
| 2009/0252392 A1* | 10/2009 | Panarace | G16H 30/20 | 382/128 |
| 2009/0288037 A1* | 11/2009 | Lawton | G06F 9/451 | 715/804 |
| 2010/0130860 A1* | 5/2010 | Yamagata | A61B 8/13 | 600/443 |
| 2011/0150336 A1* | 6/2011 | Van | G06V 30/416 | 382/182 |
| 2011/0238082 A1* | 9/2011 | Wenderow | A61M 25/0105 | 606/130 |
| 2012/0014559 A1* | 1/2012 | Suehling | G06T 7/33 | 382/128 |
| 2012/0182244 A1* | 7/2012 | Arthur | G16H 40/67 | 345/173 |
| 2012/0330680 A1* | 12/2012 | O'Larte | G06F 3/005 | 705/3 |
| 2013/0110537 A1* | 5/2013 | Smith | G06Q 10/10 | 705/2 |
| 2013/0132485 A1* | 5/2013 | Thomas | H04L 12/1822 | 709/205 |
| 2013/0188852 A1* | 7/2013 | Bakai | A61B 6/5247 | 382/128 |
| 2013/0326386 A1* | 12/2013 | Vendrell | G16H 50/30 | 715/771 |
| 2014/0098209 A1* | 4/2014 | Neff | A61B 5/742 | 348/77 |
| 2014/0282018 A1* | 9/2014 | Amble | G16H 40/63 | 715/733 |
| 2014/0294149 A1* | 10/2014 | Rieber | G06T 7/0012 | 378/62 |
| 2015/0073832 A1* | 3/2015 | Goodnow, II | G16H 10/40 | 705/2 |
| 2015/0081331 A1* | 3/2015 | Gaziano | G16H 10/60 | 705/3 |
| 2016/0062956 A1* | 3/2016 | Gotman | G06V 10/22 | 715/243 |
| 2016/0092721 A1* | 3/2016 | Kanagasingam | H04N 5/44 | 348/78 |
| 2016/0371786 A1* | 12/2016 | Kusens | G16H 10/60 | |
| 2016/0378275 A1* | 12/2016 | Akiner | G06V 30/412 | 715/762 |
| 2017/0329922 A1* | 11/2017 | Eberting | G16H 40/67 | |
| 2018/0049712 A1* | 2/2018 | Muraoka | A61B 6/461 | |
| 2018/0107792 A1* | 4/2018 | Rajan | G16H 50/20 | |
| 2018/0121843 A1* | 5/2018 | Connely, IV | G16H 40/20 | |
| 2018/0254099 A1* | 9/2018 | Beydoun | G16H 30/40 | |
| 2018/0263574 A1* | 9/2018 | Zannoli | A61B 90/361 | |
| 2018/0275836 A1* | 9/2018 | Hermans | G06F 3/0482 | |
| 2018/0350454 A1* | 12/2018 | Dorn | G16H 20/40 | |
| 2018/0374568 A1* | 12/2018 | Agnello | G06V 10/25 | |
| 2019/0059725 A1* | 2/2019 | Greiner | G16H 50/20 | |
| 2019/0080796 A1* | 3/2019 | Greiner | A61B 5/743 | |
| 2019/0089533 A1* | 3/2019 | Agnello | H04L 63/0823 | |
| 2019/0172586 A1* | 6/2019 | Choksi | G16H 10/60 | |
| 2019/0189292 A1* | 6/2019 | Shaya | H04L 63/0428 | |
| 2019/0272921 A1* | 9/2019 | Koll | G10L 15/26 | |
| 2019/0290215 A1* | 9/2019 | Gilbert | G16H 30/20 | |
| 2019/0328228 A1* | 10/2019 | Shibata | G16H 30/40 | |
| 2019/0365359 A1* | 12/2019 | Teraoka | A61B 8/565 | |
| 2020/0058390 A1* | 2/2020 | Kohle | G16H 50/70 | |
| 2020/0098473 A1* | 3/2020 | Agnello | H04L 67/06 | |
| 2020/0138397 A1* | 5/2020 | Suzuki | A61B 6/4405 | |
| 2020/0160574 A1* | 5/2020 | Nye | A61B 5/7475 | |
| 2020/0250826 A1* | 8/2020 | Cohen Maimon | G06T 17/00 | |
| 2020/0305802 A1* | 10/2020 | Archambault | A61B 5/0002 | |
| 2020/0335205 A1* | 10/2020 | Nye | G16H 30/40 | |
| 2020/0405399 A1* | 12/2020 | Steinberg | A61B 6/466 | |
| 2021/0007595 A1* | 1/2021 | Yazdi | A61B 1/0002 | |
| 2021/0035670 A1* | 2/2021 | Abrahamsson | G16H 40/20 | |
| 2021/0065889 A1* | 3/2021 | Page | G16H 40/63 | |

* cited by examiner

CAMERA VIEW AND SCREEN SCRAPING FOR INFORMATION EXTRACTION FROM IMAGING SCANNER CONSOLES

CROSS REFERENCE TO RELATED APPLICATIONS

This application claims the benefit of U.S. Provisional Patent Application No. 62/936,741 filed Nov. 18, 2019. This application is hereby incorporated by reference herein.

FIELD

The following relates generally to the imaging arts, remote imaging assistance arts, remote imaging examination monitoring arts, and related arts.

BACKGROUND

Medical imaging, such as computed tomography (CT) imaging, magnetic resonance imaging (MRI), positron emission tomography (PET) imaging, fluoroscopy imaging, and so forth, is a critical component of providing medical care, and is used in a wide range of medical fields, such as cardiology, oncology, neurology, orthopedics, to name a few. The operator of the medical imaging device used to acquire the medical images is typically a trained technician, while interpretation of the medical images is often handled by a medical specialist such as a radiologist. Interpretation of radiology reports or findings by the radiologist can be handled by the patient's general practitioner (GP) physician or another medical specialist such as a cardiologist, oncologist, orthopedic surgeon, or so forth.

The operator of a medical imaging device of a given modality (CT, MRI, PET, etc.) is often expected to be qualified to perform a wide range of different imaging procedures. For example, a cardiac imaging procedure may be very different from an imaging procedure targeting a known or suspected oncological tumor, which may be very different again from an orthopedic imaging procedure, etc. This requires the imaging device operator to be highly qualified, and preferably experienced, in a diverse range of different types of imaging procedures. Furthermore, the increased demand for medical imaging services has led to most hospitals providing medical imaging departments, and additional independent imaging laboratories that provide services on a contractual basis. This has led to strong demand for highly qualified and experienced medical imaging device operators.

Currently, a local technologist performs most of the steps in the imaging workflow, which can include preparing the patient, reviewing the procedure with the patient, reviewing the screening form, getting the patient changed, inserting the IV as needed, positioning the patient in the scanner, performing the scan, and reformatting the images. Depending on the experience of the technologist and complexity of the exam, he or she may require assistance from a senior technologist in positioning the patient, carrying out the scan, reviewing image quality, uncovering sources of artefacts, etc. Unfortunately, depending on the institution, the talent pool of its technologists, or the time of the exam, the senior technologist may not be available to help with every case where assistance is required. This may result in a scan that deviates from a standard protocol and quality standards, making diagnosis and potential follow-up challenging, or a scan that is insufficient for diagnostic interpretation by a radiologist, in which case, a patient will have to come back for a repeat scan at the expense of the imaging center, which is costly for the radiology provider.

As the demand for imaging studies is forecast to continue to grow, it would be beneficial to provide junior technologists with on-demand guidance and supervision for complex scans or technical issues. Remote radiology operations command centers have been considered to address this problem, by establishing channels of access to skilled senior technologists, who may be cost-effectively based at a single remote command center that services multiple medical institutions.

The following discloses certain improvements to overcome these problems and others.

SUMMARY

In one aspect, an apparatus provides remote assistance to a local operator of a medical imaging device disposed in a medical imaging device bay via a communication link from a remote location that is remote from the medical imaging device bay to the medical imaging device bay. The apparatus includes a workstation disposed at the remote location including at least one workstation display. At least one electronic processor is programmed to, over the course of a medical imaging examination performed using the medical imaging device: extract successive image frames from video or screen sharing of a controller display of the medical imaging device; screen-scrape information related to the medical imaging examination from the successive image frames over the course of the medical imaging examination; maintain status information on the medical imaging examination at least in part using the screen-scraped information; and output an alert perceptible at the remote location when the status information on the medical imaging examination satisfies an alert criterion.

In another aspect, a non-transitory computer readable medium stores instructions executable by at least one electronic processor for performing a method of providing remote assistance to a plurality of local operators of one or more medical imaging devices disposed in a corresponding number of medical imaging device bays via a communication link from a remote location that is remote from the medical imaging device bays to the medical imaging device bays. The method includes, over the course of medical imaging examinations using the medical imaging devices: extracting successive image frames from video or screen sharing of controller displays of the medical imaging devices; screen-scraping information related to the medical imaging examinations from the successive image frames over the course of the medical imaging examinations; maintaining status information on the medical imaging examinations at least in part using the screen-scraped information; and outputting an alert perceptible at the remote location when the status information on one or more of the medical imaging examinations satisfies an alert criterion.

In another aspect, a method for providing remote assistance to a local operator of a medical imaging device disposed in a medical imaging device bay via a communication link from a remote location that is remote from the medical imaging device bay to the medical imaging device bay includes, over the course of a medical examination: extracting successive image frames from video or screen sharing of a controller display of the medical imaging device; screen-scraping information related to the medical imaging examination from the successive image frames over the course of the medical imaging examinations; maintaining status information on the medical imaging examination at least in part using the screen-scraped information; and displaying the status information on the medical imaging examination at a workstation display.

One advantage resides in providing remote operators or radiologists with situational awareness of local imaging examination(s) which facilitates providing effective assistance to one or more local operators at different facilities.

Another advantage resides in providing remote operators or radiologists with awareness of local imaging examination(s) workflow which facilitates providing assistance to a one or more local operators at different facilities.

Another advantage resides in providing a remote operator with information about already-performed steps in a workflow in order to provide assistance for subsequent steps in the workflow.

Another advantage resides in providing a remote operator or radiologist with status information about an imaging examination based on what is displayed on the controller display of the medical imaging device.

Another advantage resides in providing a remote operator or radiologist with status information on a medical imaging examination using a standard display format that is independent of the controller display of the medical imaging device performing the medical imaging examination.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
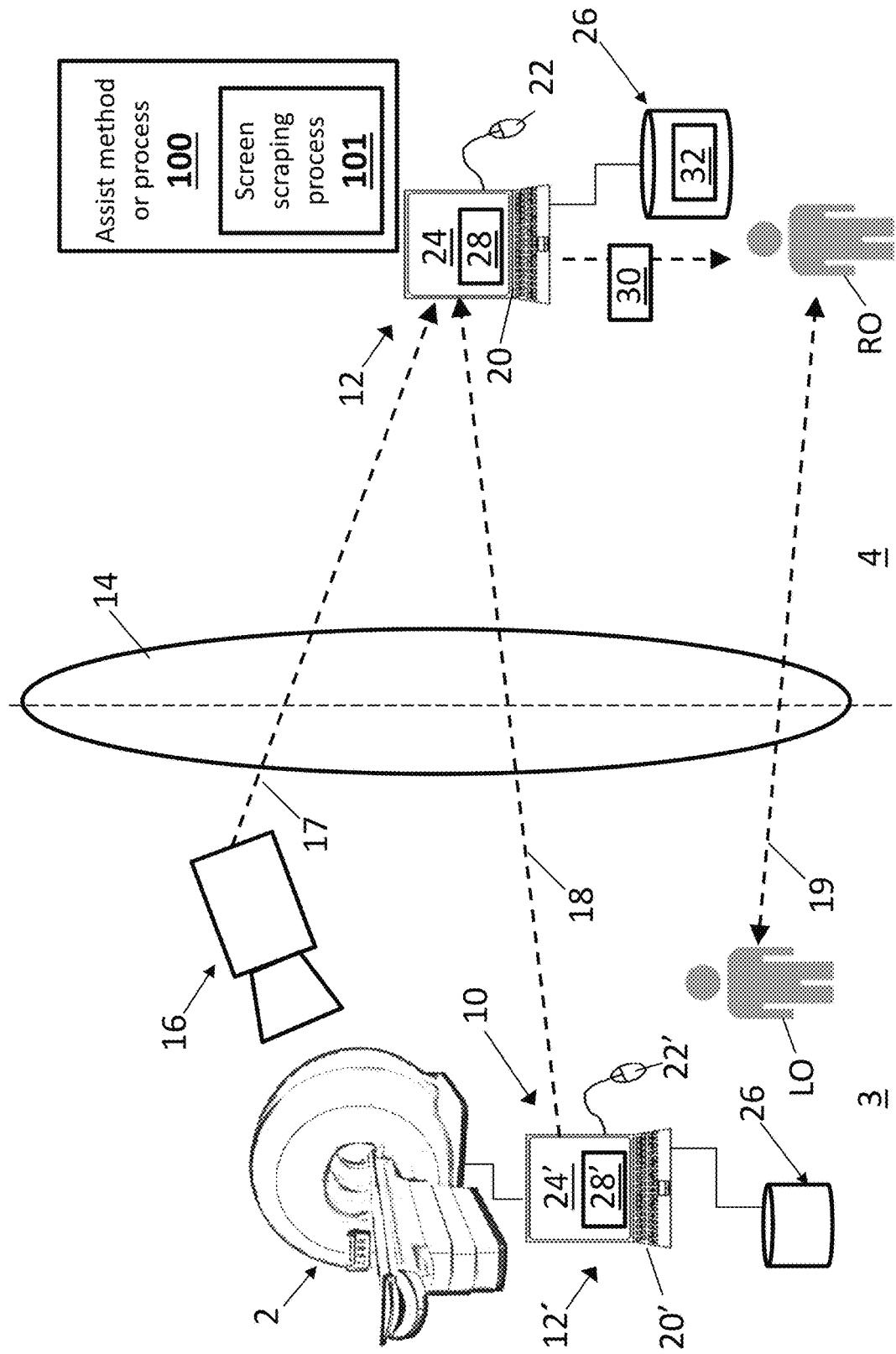
FIG. 1 diagrammatically shows an illustrative apparatus for providing remote assistance in accordance with the present disclosure.

The following relates to a remote radiology operations command center service, in which a remotely based senior technician (i.e. "super-tech") is provided with a camera view of a scanner and console rooms along with screen sharing of the console display, and can provide telephonic or other assistance to the local technician during challenging imaging examinations. The super-tech can be expected to be simultaneously handling a number of different imaging bays, and hence cannot be continuously monitoring any one imaging examination. This could create a problem if the super tech is unaware of critical information when turning attention to a particular examination. Another problem is that the super-tech may not be monitoring a particular examination during a time-critical event during which the super-tech's assistance would be valuable. The following assists the super-tech by providing the super-tech with status information about the ongoing imaging examination. The following can be additionally or alternatively employed to assist a radiologist who is tasked with performing peri-examination image review by providing the radiologist with status information about the ongoing imaging examination.

In some embodiments disclosed herein, screen scraping of the console display (and possibly or other equipment displays) can be leveraged to automatically record dynamic situational awareness, and to detect and issue alerts of events that should be brought to the super-tech's (or radiologist's) attention. Screen content may be scraped from the shared screen or from frames of a video camera whose field of view includes the screen. Using the shared screen as the source for the screen scraping can be more accurate compared with screen scraping of video, as a video camera view may be occasionally occluded by movement of personnel and may have low resolution; however, not all equipment displays will necessarily be screen-shared with the technician, in which case a camera-based screen scraping is suitable.

The scraped screen is analyzed to identify relevant information on the current status of the imaging examination, such as imaging settings or imaging sequence parameters, any alerts shown on the screen, textual labels of importance such as a textual label of the type of imaging examination being performed, and so forth. The console user interface (UI) presented on the controller display of the medical imaging device typically has a number of different dialog screens, such as examination or scan selection dialog screen(s), scan settings dialog screen(s), acquisition monitoring dialog screen(s), and so forth, each of which contain different types of information. The screen scraping is therefore performed continuously to detect when new dialog screens are accessed by the local technician and to extract the information contained in each accessed dialog screen, and to detect when (for example) the value of a particular scan setting is updated by the local technician and extract the updated value.

The presentation of the status information on the medical imaging examination obtained (at least in part) from the screen scraping may be presented at the remote radiology operations command center (and/or at a computer used by a reviewing radiologist) can optionally be vendor-agnostic, that is, the status information on the medical imaging examination can be displayed at the workstation display at the remote radiology operations command center (or radiologist's workstation) using a standard display format that is independent of the controller display (which is vendor-specific). Optionally, this standardization may extend to performing suitable unit conversion or the like so that all values obtained by the screen scraping are presented in a uniform format. For example, a time-based value may be presented by one vendor in millisecond units and by another vendor in second units, and the standardization may include converting to a vendor-agnostic choice of units.

To perform the screen scraping, a template of the set of dialog screens of the UI for the specific imaging modality and vendor/model of the imaging system is stored, and the appropriate template is used to identify the locations and content of areas of the screen (i.e. "fields") for each displayed dialog screen. Use of such vendor-, modality-, and model-specific templates enables efficient screen scraping for a wide range of medical imaging devices, thereby enabling the system to be vendor-agnostic and useable with any imaging device for which an appropriate template is available. Additionally or alternatively, optical character recognition (OCR) performed on the scraped screen can be used to identify (possibly vendor-specific) labels annotated to various types of information. For example, in a portion of an MRI settings dialog screen containing "TE=120 ms", the value may be interpreted as "time-to-echo" of 12 milliseconds based on the labels "TE" which represents "timeto-echo" and "ms" which indicates milliseconds. A vendor/model/modality-specific database of labels can be maintained, so that the display is correctly interpreted in cases in which different vendors (or models et cetera) use different labels for the same value.

In other embodiments disclosed herein, to improve efficiency of the super-tech, as previously noted, the scraped information can be displayed at the super-tech's computer in the remote center using a standardized status display that is the same for a given imaging modality regardless of the particular vendor. This facilitates the super-tech's ability to comprehend the information without needing to mentally adapt to the display format of the particular vendor. However, as knowledge of the vendor/make/model of the imaging system may be important information for the super-tech, the standard display may provide vendor/make/model information in a designated field of the standardized status display. Whenever the super-tech selects to monitor a given examination, the current standardized status display is brought up, so that the super-tech can be quickly brought up to date with the state of the examination.

In some embodiments disclosed herein, the system further includes workflow templates for various imaging examination workflows, optionally along with standard values for those workflows where available. The appropriate workflow template is retrieved based on information scraped from the console screen, or based on information otherwise provided to the remote service center (e.g., based on a schedule of examinations being supervised by the super-tech). Alert criteria are applied to the scraped information to detect critical events such as extensive editing of scan settings by the local technician, alerts or warnings or error messages issued on the console, multiply repeated imaging sequences, an imaging examination that is running excessively long, or so forth. When a critical event is detected, a human-perceptible (e.g. visual and/or audible) alert is issued to the super-tech.

In other embodiments disclosed herein, the current standardized status display may be used in other contexts. For example, if an on-call radiologist is to review images during the imaging examination, then the standardized status display may be presented to the radiologist along with the images so that the radiologist is appraised of the imaging examination status. Similarly, certain generated alerts might be additionally or alternatively sent to the on-call radiologist if the alert is of a type that could be effectively handled by the radiologist.

With reference to FIG. 1, an apparatus for providing assistance from a remote operator RO (or super-tech) to a local operator LO is shown. As shown in FIG. 1, the local operator LO, who operates a medical imaging device (also referred to as an image acquisition device, imaging device, and so forth) 2, is located in a medical imaging device bay 3, and the remote operator RO is disposed in a remote service location or center 4. It should be noted that the "remote operator" RO may not necessarily directly operate the medical imaging device 2, but rather provides assistance to the local operator LO in the form of advice, guidance, instructions, or the like. The remote location 4 can be a remote service center, a radiologist's office, a radiology department, and so forth. The remote location 4 may be in the same building as the medical imaging device bay 3 (this may commonly be the case, for example, in the case of a "remote operator" RO who is a radiologist tasked with peri-examination image review), but more typically the remote service center 4 and the medical imaging device bay 3 are in different buildings, and indeed may be located in different cities, different countries, and/or different continents. In general, the remote location 4 is remote from the imaging device bay 3 in the sense that the remote operator RO cannot directly visually observe the imaging device 2 in the imaging device bay 3 (hence optionally providing a video feed as described further herein).

The image acquisition device 2 can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 2 may also be a hybrid imaging device such as a PET/CT or SPECT/CT imaging system. While a single image acquisition device 2 is shown by way of illustration in FIG. 1, more typically a medical imaging laboratory will have multiple image acquisition devices, which may be of the same and/or different imaging modalities. For example, if a hospital performs many CT imaging examinations and relatively fewer MRI examinations and still fewer PET examinations, then the hospital's imaging laboratory (sometimes called the "radiology lab" or some other similar nomenclature) may have three CT scanners, two MRI scanners, and only a single PET scanner. This is merely an example. Moreover, the remote service center 4 may provide service to multiple hospitals. The local operator controls the medical imaging device 2 via an imaging device controller 10. The remote operator is stationed at a remote workstation 12 (or, more generally, an electronic controller 12).

As used herein, the term "medical imaging device bay" (and variants thereof) refer to a room containing the medical imaging device 2 and also any adjacent control room containing the medical imaging device controller 10 for controlling the medical imaging device. For example, in reference to an MRI device, the medical imaging device bay 3 can include the radiofrequency (RF) shielded room containing the MRI device 2, as well as an adjacent control room housing the medical imaging device controller 10, as understood in the art of MRI devices and procedures. On the other hand, for other imaging modalities such as CT, the imaging device controller 10 may be located in the same room as the imaging device 2, so that there is no adjacent control room and the medical bay 3 is only the room containing the medical imaging device 2. In addition, while FIG. 1 shows a single medical imaging device bay 3, it will be appreciated that the remote service center 4 (and more particularly the remote workstation 12) is in communication with multiple medical bays via a communication link 14, which typically comprises the Internet augmented by local area networks at the remote operator RO and local operator LO ends for electronic data communications.

As diagrammatically shown in FIG. 1, a camera 16 (e.g., a video camera) is arranged to acquire a video stream 17 of a portion of the medical imaging device bay 3 that includes at least the area of the imaging device 2 where the local operator LO interacts with the patient, and optionally may further include the imaging device controller 10. The video stream 17 is sent to the remote workstation 12 via the communication link 14, e.g. as a streaming video feed received via a secure Internet link. Additionally, a screen mirroring data stream 18 is sent from the imaging device controller 10 to the remote workstation 12. The communication link 14 also provides a natural language communication pathway 19 for verbal and/or textual communication between the local operator and the remote operator. For example, the natural language communication link 19 may be a Voice-Over-Internet-Protocol (VOIP) telephonic connection, an online video chat link, a computerized instant messaging service, or so forth. Alternatively, the natural language communication pathway 19 may be provided by a dedicated communication link that is separate from the communication link 14 providing the data communications 17, 18, e.g. the natural language communication pathway 19 may be provided via a landline telephone.

FIG. 1 also shows, in the remote service center 4 including the remote workstation 12, such as an electronic processing device, a workstation computer, or more generally a computer, which is operatively connected to receive and present the video 17 of the medical imaging device bay 3 from the camera 16 and to present the screen mirroring data stream 18 as a mirrored screen. Additionally or alternatively, the remote workstation 12 can be embodied as a server computer or a plurality of server computers, e.g. interconnected to form a server cluster, cloud computing resource, or so forth. The workstation 12 includes typical components, such as an electronic processor 20 (e.g., a microprocessor), at least one user input device (e.g., a mouse, a keyboard, a trackball, and/or the like) 22, and at least one display device 24 (e.g. an LCD display, plasma display, cathode ray tube display, and/or so forth). In some embodiments, the display device 24 can be a separate component from the workstation 12. The display device 24 may also comprise two or more display devices, e.g. one display presenting the video 17 and the other display presenting the shared screen of the imaging device controller 10 generated from the screen mirroring data stream 18. Alternatively, the video and the shared screen may be presented on a single display in respective windows. The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 12, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the remote operator display device 24.

The medical imaging device controller 10 in the medical imaging device bay 3 also includes similar components as the remote workstation 12 disposed in the remote service center 4. Except as otherwise indicated herein, features of the medical imaging device controller 10, which includes a local workstation 12', disposed in the medical imaging device bay 3 similar to those of the remote workstation 12 disposed in the remote service center 4 have a common reference number followed by a "prime" symbol, and the description of the components of the medical imaging device controller 10 will not be repeated. In particular, the medical imaging device controller 10 is configured to display a GUI 28' on a display device or controller display 24' that presents information pertaining to the control of the medical imaging device 2, such as configuration displays for adjusting configuration settings an alert 30 perceptible at the remote location when the status information on the medical imaging examination satisfies an alert criterion of the imaging device 2, imaging acquisition monitoring information, presentation of acquired medical images, and so forth. It will be appreciated that the screen mirroring data stream 18 carries the content presented on the display device 24' of the medical imaging device controller 10. The communication link 14 allows for screen sharing between the display device 24 in the remote service center 4 and the display device 24' in the medical imaging device bay 3. The GUI 28' includes one or more dialog screens, including, for example, an examination/scan selection dialog screen, a scan settings dialog screen, an acquisition monitoring dialog screen, among others. The GUI 28' can be included in the video feed 17 or the mirroring data stream 17' and displayed on the remote workstation display 24 at the remote location 4.

The remote workstation 12 is configured as described above to perform a method or process 100 for providing assistance the local operator LO. The method or process 100 includes a screen sharing process 101 which performs screen scraping on the controller display 24' of the medical imaging device 2, and the method or process 100 includes maintaining status information on the ongoing medical imaging examination based on information obtained by the screen scraping 101. The screen scraping process 101 operates to extract (from the video 17 or the screen sharing 18) successive image frames of the controller display 24' of the medical imaging device 2, and to screen-scrape information related to the medical imaging examination from the successive image frames over the course of the medical imaging examination. The non-transitory storage medium 26 stores instructions which are readable and executable by the at least one electronic processor 20 (of the workstation 12, as shown, and/or the electronic processor or processors of a server or servers on a local area network or the Internet) to perform disclosed operations including performing the method or process 100. In some examples, the method 100 may be performed at least in part by cloud processing. In particular, the GUI 28 presented on the display 24 of the remote workstation 12 preferably includes a window presenting the video 17, and a window presenting the mirrored screen of the medical imaging device controller 10 constructed from the screen mirroring data stream 18, and status information on the medical imaging examination that is maintained at least in part using the screen-scraped information. This allows the remote operator RO to be aware of the content of the display of the medical imaging device controller 10 (via the shared screen) and also to be aware of the physical situation, e.g. position of the patient in the medical imaging device 2 (via the video 17), and to additionally be aware of the status of the imaging examination as summarized by the status information. During an imaging procedure, the natural language communication pathway 19 is suitably used to allow the local operator LO and the remote operator RO to discuss the procedure and in particular to allow the remote operator to provide advice to the local operator.

Figure 2:
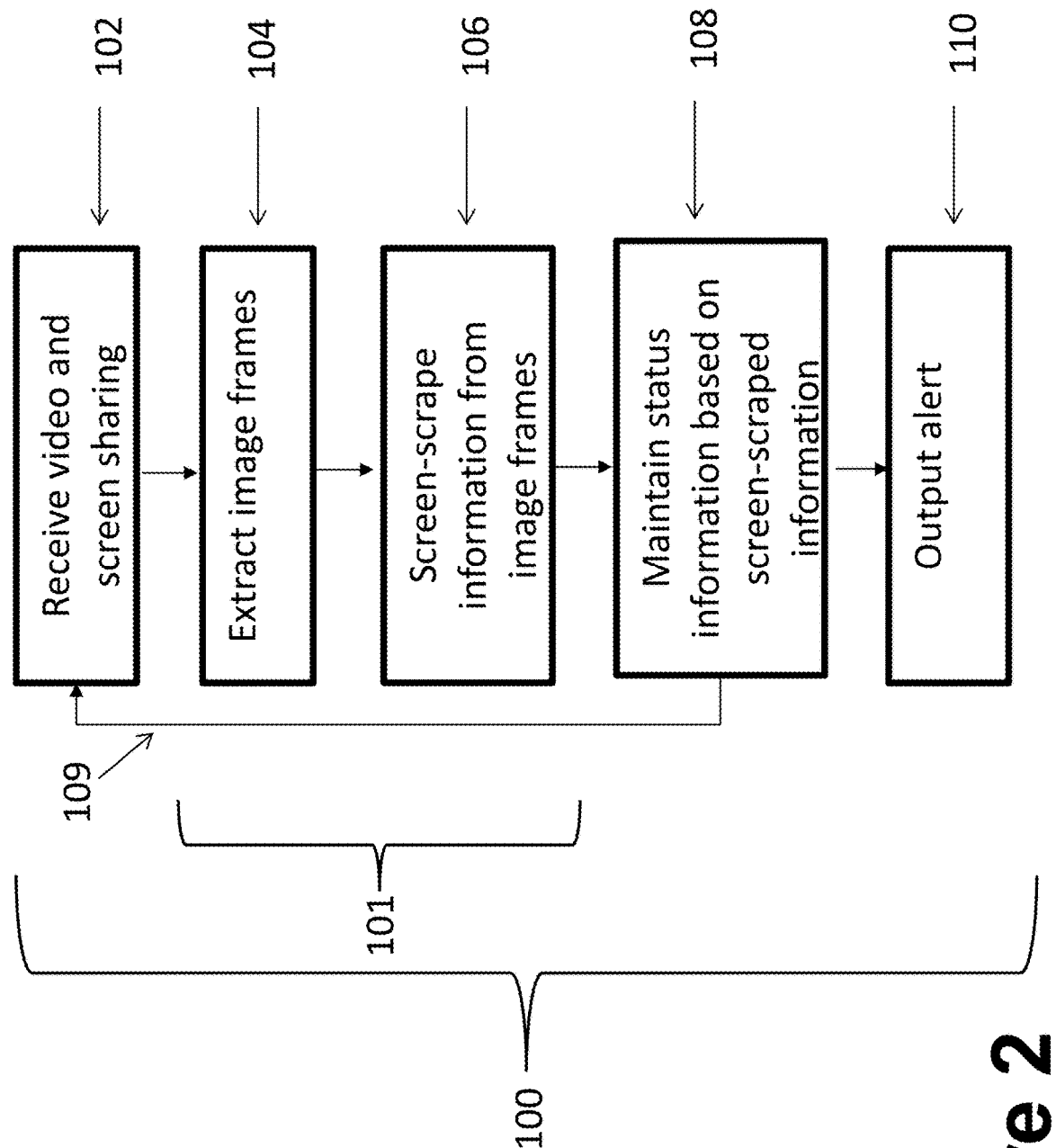
FIG. 2 shows an example flow chart of operations suitably performed by the apparatus of FIG. 1.

With reference to FIG. 2, and with continuing reference to FIG. 1, an illustrative embodiment of the method 100 is diagrammatically shown as a flowchart. The method 100 is performed over the course of a medical imaging examination performed using the medical imaging device 2. At an operation 102, the at least one electronic processor 20 of the workstation 12 in the remote location 4 is programmed to receive at least one of: video 17 from the video camera 16 of the medical imaging device 2 located in the medical imaging device bay 3; and/or the screen sharing 18. The video feed 17 and/or the screen sharing 18 can be displayed at the remote workstation display 24, typically in separate windows of the GUI 28.

At an operation 104, the at least one electronic processor 20 of the workstation 12 in the remote location 4 is programmed to extract successive image frames from the video 17 or from the screen sharing 18 of the controller display 24' of the medical imaging device 2. The extracted successive frames may not necessarily include every image frame of the acquired video or screen sharing. For example, the video or screen sharing might be at 30 frames per sec (fps), but the screen scraping might only be able to process 5 fps due to computational limitations. In that case, the successive image frames might be every sixth video frame. The extracted successive frames are bitmap images. These bitmap images may be color or monochrome images, depending on the source video 17 or screen sharing 18 and, in the case of color video or screen sharing, depending on whether the extraction operation 104 retains the color information. The extracted successive frames contain information such as details of the imaging protocol being acquired, aborted or repeated image sequences, an amount of time left in the medical exam, error messages generated by the imaging device 2, patient breathing, heart rate waveforms, a patient screening form, and so forth. However, the information is contained in bitmap image form, and hence is not readily machine interpretable.

Accordingly, at an operation 106, the at least one electronic processor 20 of the workstation 12 in the remote location 4 is programmed to screen-scrape information related to the medical imaging examination from the extracted successive image frames over the course of the medical imaging examination (although this operation may take place in the medical device imaging bay 3 and transmitted to the remote location). The extraction and screen scraping operations 104, 106 correspond to the screen-scrapping process 101 of FIG. 1. At an operation 108, the at least one electronic processor 20 is programmed to maintain status information on the medical imaging examination at least in part using the screen-scraped information. As diagrammatically indicated by looping arrow 109, the operations 102, 104, 106, 108 are repeated in iterative fashion over the course of a medical imaging examination performed using the medical imaging device 2 in order to maintain real time current status information generated at operation 108. During a routine imaging examination, or during routine portions of an imaging examination, the maintained status information will indicate the imaging examination is progressing favorably, and is unlikely to benefit from intervention by the remote operator RO. This is advantageous, because in many practical situations the remote operator RO may be tasked with assisting a number of ongoing imaging examinations concurrently, and cannot continuously monitor all of the simultaneous imaging examinations tasked to the remote operator RO. However, the maintained status information can provide information indicating that there is a problem with the imaging examination, or may detect some other situation such as a warning displayed on the controller display 24', which indicates that intervention by the remote operator RO may be advantageous. Accordingly, at an operation 110, the at least one electronic processor 20 of the workstation 12 in the remote location 4 is programmed to output an alert 30 perceptible at the remote location when the status information on the medical imaging examination satisfies an alert criterion (or, some other alert criterion is met, such as detecting a warning displayed on the controller display 24' via the screen scraping 101).

The information screen-scraped in the operation 106 from the image frames extracted in the operation 104 can include a variety of information. Although described below in terms of a single imaging device bay 3, the at least one electronic processor 20 can be iteratively executing a plurality of instances of the operations 104, 106 to screen-scrape video 17 (or screen-sharing 18) of a corresponding plurality of medical imaging devices 2 disposed at a corresponding number of medical imaging devices bays 3.

The operations 106-110 can be performed in a variety of manners, not necessarily being mutually exclusive. In one example, the screen scraping of information 106 detects when the successive image frames depict a change to a new dialog screen on the GUI 28' presented on the controller display 24'. That is, the local operator LO is operating the medical imaging device 12 using the dialog screens on the GUI 28'. The GUI 28' is captured in the successive image frames. The screen-scraping operation 106 then includes screen-scraping at least a portion of the information from one or more of the successive image frames that depict the new dialog screen.

In another example, the screen scraping of information 106 detects a new setting value for the medical imaging examination in the successive image frames. That is, the local operator LO adjust a setting value on the GUI 28' of the controller display 24'. The GUI 28', with this updated setting value, is captured in the successive image frames. The screen-scraping operation 106 then includes screen-scraping the new setting value from one or more imaging frames of the successive image frames that depict the new setting value. The maintaining operation 108 includes updating the status information on the medical imaging examination on the workstation display 24 with the screen-scraped new setting value.

In a further example, the screen scraping of information 106 identifies one or more dialog screens in the GUI 28' of the controller display 24' in the successive image frames. The workstation 12 then retrieves a dialog screen template 32 from a database stored on the non-transitory computer readable medium 26. The template 32 corresponds to a dialog screen depicted in in one or more of the image frames, and the template is usually one of a set of dialog screen templates for the GUI 28' of the vendor/make/model of the medical imaging device 2. By providing dialog screen template sets for various GUIs of various imaging devices available from a range of vendors, the system can operate in conjunction with imaging devices of a wide range of different imaging modalities made by different vendors. The template 32 identifies one or more screen regions in the GUI 28', and associates the one or more screen regions with settings of the medical imaging examination. The screen-scraping operation 106 includes screen-scraping information from an image frame under analysis by the remote operator RO in one or more screen regions. The screen-scraped information is then associated with settings of the medical imaging examination using the associations provided by the corresponding dialog screen template 32.

In yet another example, one of the image frames under analysis by the screen scraping of information 106 is screen-scraped using OCR to extract a value and one or more labels proximate to the value in the image frame under analysis. The remote workstation 12 then identifies a current setting value for the medical imaging examination by associating the screen-scraped value with a setting of the medical imaging examination based on the screen-scraped one or more labels that are positioned proximate to the value in the image frame under analysis. For example, if the screen-scraped portion of the image frame includes a setting "TE=120 ms", the value may be interpreted as "time-to-echo" of 120 milliseconds based on the labels "TE" which represents "time-to-echo" and "ms" which indicates milliseconds. The maintaining operation 108 then includes updating the status information on the medical imaging examination on the workstation display 24 with the screen-scraped current setting value.

In another example, one of the image frames under analysis by the remote operator RO is screen-scraped to detect an error or warning message depicted on the controller display 24' of the medical imaging device 2. The output operation 110 includes outputting an alert 30 perceptible at the remote location 4 (e.g., visually displayed on the workstation display 24, audibly output with a speaker (not shown), and so forth) when the detected error or warning messages satisfies an error or warning alert criterion. In one approach, the set of templates 32 include templates for most or all error or warning messages that can be issued by the GUI 28' of the imaging device 2, and the detection of the error or warning message entails matching the screen scraped error or warning message with the template. Such matching could be done in image space, where the error or warning message templates 32 are images, or could be done after OCR screen scrapes the text of the error or warning message, in which case the matching entails matching the OCR'd error or warning text with textual templates 32.

In yet a further example, the screen-scraping operation 106 includes performing OCR processes on an image frame under analysis by the remote operator RO to extract textual information.

The maintaining operation 108 looped over the course of the imaging examination as indicated by a loop 109, operates to maintain current status information on the medical imaging examination at least in part using the screen-scraped information. A portion of the status information may also be obtained from other sources, such as from direct machine-readable communication with the device controller 10 of the medical imaging device 2. In some embodiments, the status information is displayed on the workstation display 24, along with the screen-scraped information. For example, the status information can be displayed using a standard display format that is independent of the controller display 24'. The standard display format can include a display of a vendor of the medical imaging device 2, along with optionally including a make and model of the medical imaging device.

At the operation 110, the alert 30 is output when the status information on the medical imaging examination satisfies an alert criterion. To do so, in one example, the status information is compared with information in one or more workflow templates 32 retrieved based on the information screen-scraped in the operation 106. The alert 30 can be output when this comparison of the status information with the information in the templates 32 satisfies the alert criterion (e.g., an echo time in the status information being above or below a threshold listed in the template(s)). In another example, setting values shown in the status information are compared with corresponding values in the template(s) 32, and the alert 30 is output when one or more of the values is outside a range of corresponding values in the information of the template (s) 32. In a further example, the alert 30 is output when the alert criterion based on the status information indicates significant changes in the imaging examination, such as extensive editing of scan settings on the GUI 28' by the local operator LO, the local operator multiple-repeating imaging sequences, an imaging session running excessively long, and so forth.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus for providing remote assistance to a local operator of a medical imaging device disposed in a medical imaging device bay via a communication link from a remote location that is remote from the medical imaging device bay to the medical imaging device bay, the apparatus comprising:
　a workstation disposed at the remote location including at least one workstation display;
　a natural communication pathway between the local operator and a remote operator located in the remote location; and
　at least one electronic processor programmed to, over the course of a medical imaging examination performed using the medical imaging device:
　　extract successive image frames from video or screen sharing of a controller display of the medical imaging device;
　　screen-scrape information related to one or more settings of the medical imaging device used in the medical imaging examination from the successive image frames over the course of the medical imaging examination, the one or more settings of the medical imaging device including one or more of an examination dialog screen, a scan selection dialog screen, a scan settings dialog screen, or an acquisition monitoring dialog screen;
　　maintain status information on the medical imaging examination at least in part using the screen-scraped information; and
　　output an alert perceptible at the remote location when the status information on the medical imaging examination satisfies an alert criterion.

2. The apparatus according to claim 1, wherein the screen-scrape of information includes:
　detecting when the successive image frames depict a change to a new dialog screen presented on the controller display; and
　screen-scraping at least a portion of the information from one or more of the successive image frames that depict the new dialog screen.

3. The apparatus according to claim 1, wherein the screen scrape of information includes:
　detecting a new setting value for the medical imaging examination in the successive image frames; and
　screen-scraping the new setting value from one or more imaging frames of the successive image frames that depict the new setting value;
　wherein the status information on the medical imaging examination is updated with the screen-scraped new setting value.

4. The apparatus according to claim 1, wherein the screen-scrape of information includes:
　identifying a corresponding dialog screen template that corresponds to a dialog screen depicted in an image frame under analysis of the successive image frames wherein the corresponding dialog screen template identifies one or more screen regions and associates the one or more screen regions with settings of the medical imaging examination; and screen-scraping information from the image frame under analysis in the one or more screen regions and associating the screen-scraped information in the one or more screen regions with settings of the medical imaging examination using the associations provided by the corresponding dialog screen template.

5. The apparatus according to claim 1, wherein the screen-scrape of information includes:

screen scraping an image frame under analysis of the successive image frames to extract a value and one or more labels that are positioned proximate to the value in the image frame under analysis; and identifying a current setting value for the medical imaging examination by associating the screen-scraped value with a setting of the medical imaging examination based on the screen-scraped one or more labels that are positioned proximate to the value in the image frame under analysis;

wherein the status information on the medical imaging examination is updated with the current setting value.

6. The apparatus according to claim 1, wherein the screen-scrape of information includes:

screen scraping an image frame under analysis of the successive image frames to detect an error or warning message depicted on the display screen of the medical imaging device;

wherein the at least one electronic processor is further programmed to output an alert perceptible at the remote location when the detected error or warning message satisfies an error or warning alert criterion.

7. The apparatus according to claim 1, wherein the screen-scrape of information includes:

performing optical character recognition (OCR) on an image frame under analysis of the successive image frames to extract textual information.

8. The apparatus according to claim 1, wherein the at least one electronic processor is further programmed to:

perform screen sharing in which the controller display of the medical imaging device is shared at the workstation display;

wherein the extraction of the successive image frames comprises extraction of the successive image frames from the screen sharing of the controller display of the medical imaging device at the workstation at the remote location.

9. The apparatus according to claim 1, wherein the at least one electronic processor is further programmed to:

receive a video feed capturing the controller display of the medical imaging device; and display the video feed at the workstation display;

wherein the extraction of the successive image frames comprises extraction of the successive image frames from the received video feed.

10. The apparatus according to claim 9, wherein the at least one electronic processor is programmed to display images acquired by the medical imaging device during the medical imaging examination at the workstation display.

11. The apparatus according to claim 1, wherein the at least one electronic processor is further programmed to:

display the status information on the medical imaging examination at the workstation display.

12. The apparatus according to claim 11, wherein the at least one electronic processor is programmed to display the status information on the medical imaging examination at the workstation display using a standard display format that is independent of the controller display.

13. The apparatus according to claim 12, wherein the standard display format further includes a display of at least a vendor of the medical imaging device.

14. The apparatus according to claim 1, wherein the at least one electronic processor is programmed to:

retrieve at least one workflow template based on the information extracted from the screen-scraped video;

compare the status information on the medical imaging examination with information in the retrieved at least one workflow template; and wherein the alert criterion is based on the comparison of the status information on the medical imaging examination with the information in the retrieved at least one workflow template.

15. The apparatus according to claim 14, wherein the at least one electronic processor is programmed to:

compare the status information on the medical imaging examination with corresponding values of the information in the at least one workflow template; and wherein the alert criterion is based on the status information on the medical imaging examination being outside a range of values of the information in the at least one workflow template.

16. The apparatus according to claim 14, wherein the alert criterion is based on the maintained status information on the medical imaging examination indicating one or more of:

extensive editing of scan settings by the local operator;

multiply-repeated imaging sequences; and/or an imaging session running excessively long.

17. The apparatus according to claim 1, wherein the at least one electronic processor is programmed to screen-scrape video of a plurality of medical imaging devices disposed at a corresponding number of medical imaging device bays.

18. A non-transitory computer readable medium storing instructions executable by at least one electronic processor for performing a method of providing remote assistance to a plurality of local operators of one or more medical imaging devices disposed in a corresponding number of medical imaging device bays via a communication link from a remote location that is remote from the medical imaging device bays to the medical imaging device bays, the method comprising, over the course of medical imaging examinations using the medical imaging devices:

extracting successive image frames from video or screen sharing of controller displays of the medical imaging devices;

screen-scraping information related to one or more settings of the medical imaging devices used in the medical imaging examinations from the successive image frames over the course of the medical imaging examinations, the one or more settings of the medical imaging devices including one or more of an examination dialog screen, a scan selection dialog screen, a scan settings dialog screen, or an acquisition monitoring dialog screen;

maintaining status information on the medical imaging examinations at least in part using the screen-scraped information;

retrieving from a database, at least one workflow template based on the information extracted from the screen-scraped video;

comparing the status information on the medical imaging examinations with information in the retrieved at least one workflow template; and outputting an alert perceptible at the remote location when the status information on one or more of the medical imaging examinations satisfies an alert criterion.

19. The non-transitory computer readable medium according to claim 18,
wherein the alert criterion is based on the comparison of the status information on the medical imaging examination with the information in the retrieved at least one workflow template.

20. A method for providing remote assistance to a local operator of a medical imaging device disposed in a medical imaging device bay via a communication link from a remote location that is remote from the medical imaging device bay to the medical imaging device bay, the method comprising, over the course of a medical imaging examination:

extracting successive image frames from video or screen sharing of a controller display of the medical imaging device;

screen-scraping information related to one or more settings of the medical imaging device used in the medical imaging examination from the successive image frames over the course of the medical imaging examination, the one or more settings of the medical imaging device including one or more of an examination dialog screen, a scan selection dialog screen, a scan settings dialog screen, or an acquisition monitoring dialog screen;

maintaining status information on the medical imaging examination at least in part using the screen-scraped information; and displaying the status information on the medical imaging examination at a workstation display.

\* \* \* \* \*